US010905354B2

(12) United States Patent
Sakashita

(10) Patent No.: US 10,905,354 B2
(45) Date of Patent: Feb. 2, 2021

(54) MRI APPARATUS

(71) Applicant: Canon Medical Systems Corporation, Otawara (JP)

(72) Inventor: Naotaka Sakashita, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 13 days.

(21) Appl. No.: 16/520,400

(22) Filed: Jul. 24, 2019

(65) Prior Publication Data

US 2020/0037918 A1    Feb. 6, 2020

(30) Foreign Application Priority Data

Aug. 2, 2018  (JP) .................................. 2018-146004

(51) Int. Cl.
| | |
|---|---|
| *A61B 5/055* | (2006.01) |
| *G01R 33/50* | (2006.01) |
| *G01R 33/56* | (2006.01) |
| *G01R 33/38* | (2006.01) |
| *G01R 33/565* | (2006.01) |

(52) U.S. Cl.
CPC .............. *A61B 5/055* (2013.01); *G01R 33/50* (2013.01); *G01R 33/5607* (2013.01); *G01R 33/3808* (2013.01); *G01R 33/565* (2013.01); *G06T 2207/10088* (2013.01)

(58) Field of Classification Search
CPC .... A61B 5/055; G01R 33/50; G01R 33/5607; G01R 33/3808; G01R 33/565; G06T 2207/10088
See application file for complete search history.

(56) References Cited

U.S. PATENT DOCUMENTS

| | | | |
|---|---|---|---|
| 9,201,129 B2 | 12/2015 | Ikedo et al. | |
| 2015/0362575 A1* | 12/2015 | Ourselin | G01R 33/5616 382/131 |
| 2017/0097399 A1 | 4/2017 | Shiodera et al. | |
| 2018/0024216 A1* | 1/2018 | Gilbert | G01R 33/5635 324/309 |
| 2018/0259607 A1* | 9/2018 | Liu | G01R 33/243 |

FOREIGN PATENT DOCUMENTS

| | | |
|---|---|---|
| JP | 2012-86056 A | 5/2012 |
| JP | 5619339 B2 | 11/2014 |
| JP | 2017-70386 A | 4/2017 |

* cited by examiner

*Primary Examiner* — Gregory H Curran
(74) *Attorney, Agent, or Firm* — Oblon, McClelland, Maier & Neustadt, L.L.P.

(57) ABSTRACT

In one embodiment, an MRI apparatus includes a memory storing a predetermined program and processing circuitry. The processing circuitry is configured, by executing the predetermined program, to generate a first image having a first phase affected by susceptibility, generate a second image having a second phase affected by both of the susceptibility and flow, and distinguish difference in susceptibility or flow for a pixel of a third image by using the first phase and the second phase or by using a value calculated from the first phase and a value calculated from the first phase, the third image having regions which are substantially same in contrast.

17 Claims, 12 Drawing Sheets

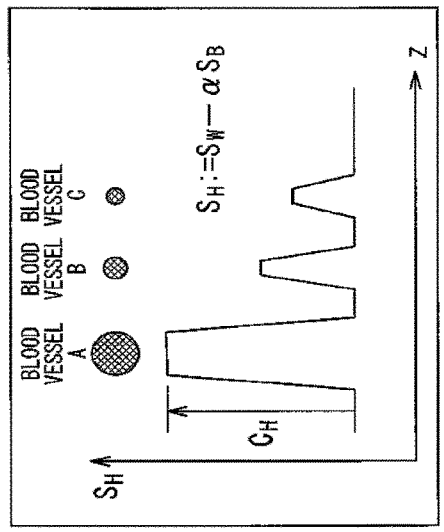
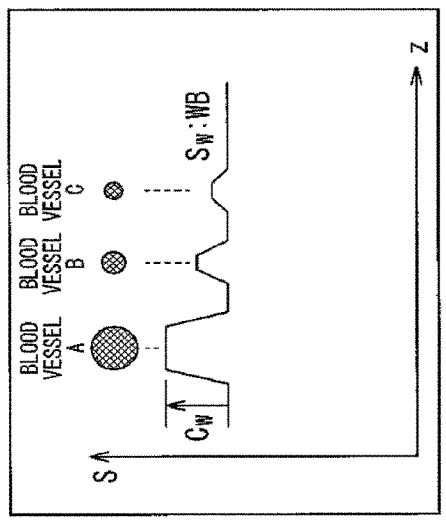
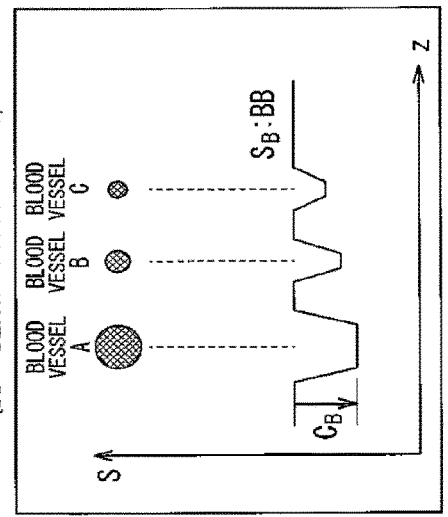

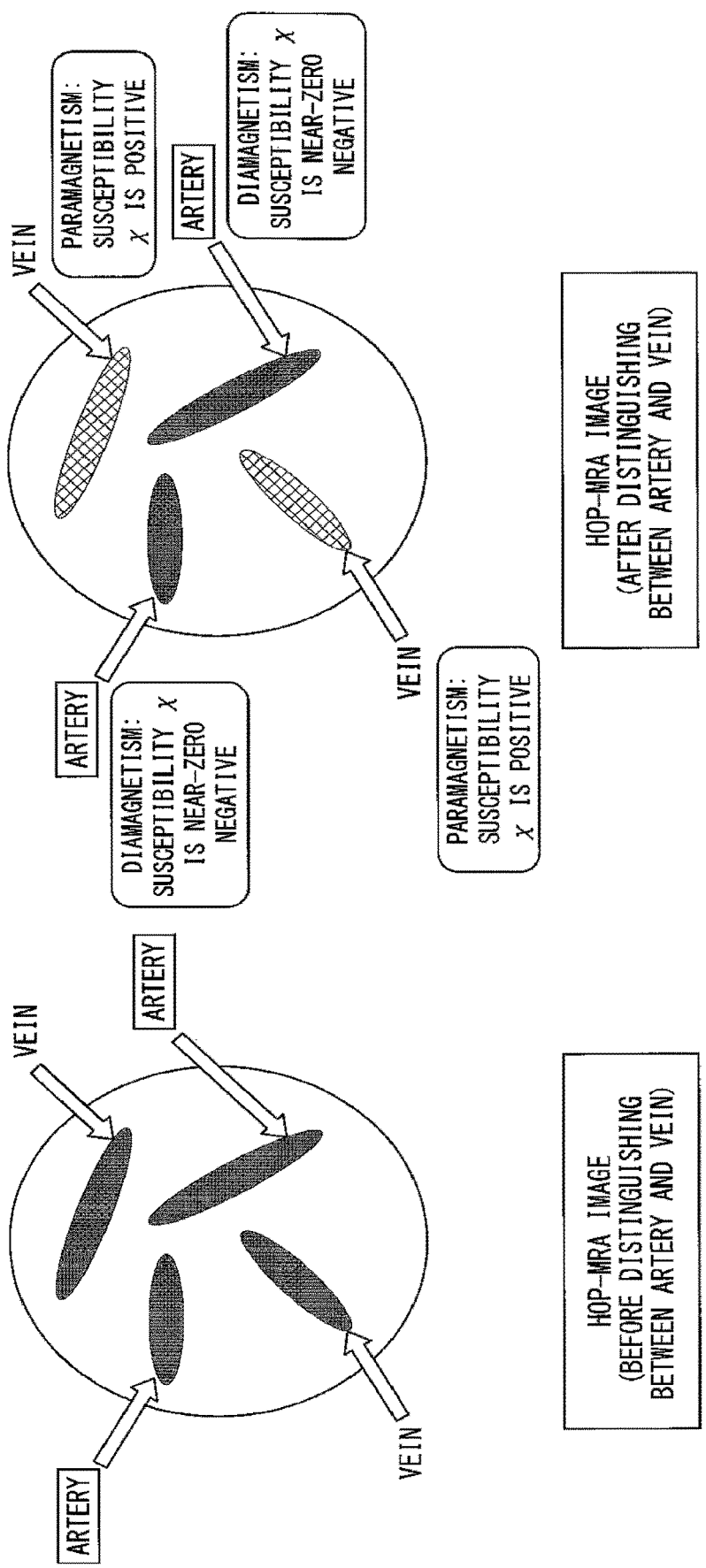

US 10,905,354 B2

MRI APPARATUS

CROSS-REFERENCE TO RELATED APPLICATION

This application is based upon and claims the benefit of priority from Japanese Patent Application No. 2018-146004, filed on Aug. 2, 2018, the entire contents of which are incorporated herein by reference.

FIELD

Embodiments described herein relate generally to a magnetic resonance imaging (MRI) apparatus.

BACKGROUND

An MRI apparatus is an imaging apparatus that magnetically excites nuclear spin of an object placed in a static magnetic field by applying a radio frequency (RF) pulse having the Larmor frequency and reconstructs an image on the basis of magnetic resonance (MR) signals emitted from the object due to the excitation.

Of imaging methods using an MRI apparatus, the White Blood method is known as a method in which fast blood flow such as an artery is depicted as a strong signal by using an inflow effect of blood, and the Black Blood method is known as a method in which blood vessels are depicted as weaker signals than the signals of the background by actively enhancing dephasing due to blood flow. There is also known an imaging method in which both of arteries and veins are depicted with high contrast by combining the White Blood method and the Black Blood method.

If the arteries and veins can be distinguished from each other in such an image in which the arteries and veins are both satisfactorily depicted, more useful diagnostic information can be provided.

Further, in T2*-weighted images (T2* indicates apparent transverse relaxation time), for example, it is known that veins and microbleeds are depicted as low signals having almost the same intensity. In such an image, if the veins and microbleeds can be distinguished from each other, more useful diagnostic information also can be provided.

BRIEF DESCRIPTION OF THE DRAWINGS

In the accompanying drawings:

FIG. 11A to FIG. 11C are schematic diagrams illustrating the concept of generating the third image (HOP-MRA image); and FIG. 12A and FIG. 12B are schematic diagrams illustrating the effects obtained by the MRI apparatus according to the second embodiment.

DETAILED DESCRIPTION

Hereinbelow, respective embodiments of MRI apparatuses will be described by referring to the accompanying drawings. In the following embodiments, components assigned with the same reference sign are assumed to function and operate in the same manner, and duplicate description is omitted.

In one embodiment, an MRI apparatus includes a memory storing a predetermined program and processing circuitry. The processing circuitry is configured, by executing the program, to generate a first image having a first phase affected by magnetic susceptibility (hereinafter, shortly referred to as susceptibility), generate a second image having a second phase affected by both of the susceptibility and flow, and distinguish difference in susceptibility or flow for a pixel of a third image by using the first phase and the second phase or by using a value calculated from the first phase and a value calculated from the second phase, the third image having regions which are substantially same in contrast.

Figure 1:
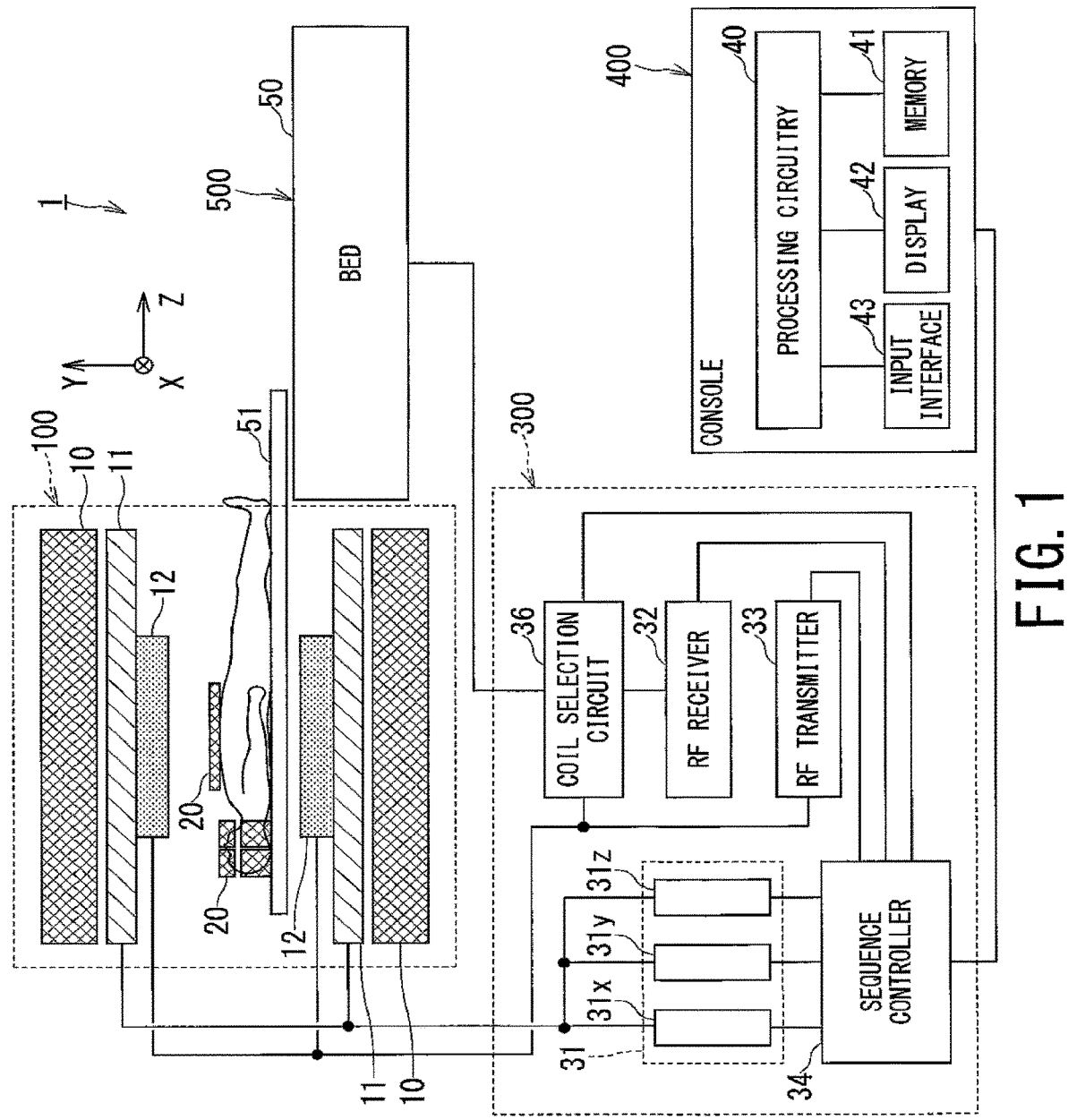
FIG. 1 is a block diagram illustrating overall configuration of the MRI apparatus according to each of the first and second embodiments.

FIG. 1 is a block diagram illustrating overall configuration of an MRI apparatus 1 according to each of the first and second embodiments. The MRI apparatus 1 includes a gantry 100, a control cabinet 300, a console 400, a bed 500, and radio frequency (RF) coils 20. The gantry 100, the control cabinet 300, and the bed 500 constitute a scanner, i.e., an imaging unit.

The gantry 100 includes a static magnetic field magnet 10, a gradient coil 11, and a whole body (WB) coil 12, and these components are housed in a cylindrical housing. The bed 500 includes a bed body 50 and a table 51.

The control cabinet 300 includes three gradient coil power supplies 31 (31x for an X-axis, 31y for a Y-axis, and 31z for a Z-axis), a coil selection circuit 36, an RF receiver 32, an RF transmitter 33, and a sequence controller 34.

The console 400 includes processing circuitry 40, a memory 41, a display 42, and an input interface 43. The console 400 functions as a host computer.

The static magnetic field magnet 10 of the gantry 100 is substantially in the form of a cylinder and generates a static magnetic field inside a bore into which an object such as a patient is transported. The bore is a space inside the cylindrical structure of the gantry 100. The static magnetic field magnet 10 includes a superconducting coil inside, and the superconducting coil is cooled down to an extremely low temperature by liquid helium. The static magnetic field magnet 10 generates a static magnetic field by supplying the superconducting coil with an electric current provided from a static magnetic field power supply (not shown) in an excitation mode. Afterward, the static magnetic field magnet 10 shifts to a permanent current mode, and the static magnetic field power supply is separated. Once it enters the permanent current mode, the static magnetic field magnet 10 continues to generate a strong static magnetic field for a long time, for example, over one year. In FIG. 1, the black circle on the chest of the object indicate the magnetic field center.

The gradient coil 11 is also substantially in the form of a cylinder and is fixed to the inside of the static magnetic field magnet 10. This gradient coil 11 applies gradient magnetic fields (for example, gradient pulses) to the object in the respective directions of the X-axis, the Y-axis, and the Z-axis, by using electric currents supplied from the gradient coil power supplies 31x, 31y, and 31z.

The bed body 50 of the bed 500 can move the table 51 in the vertical direction and in the horizontal direction. The bed body 50 moves the table 51 with an object placed thereon to a predetermined height before imaging. Afterward, when the object is imaged, the bed body 50 moves the table 51 in the horizontal direction so as to move the object to the inside of the bore.

The WB body coil 12 is shaped substantially in the form of a cylinder so as to surround the object and is fixed to the inside of the gradient coil 11. The WB coil 12 applies RF pulses transmitted from the RF transmitter 33 to the object. Further, the WB coil 12 receives magnetic resonance signals, i.e., MR signals emitted from the object due to excitation of hydrogen nuclei.

The MRI apparatus 1 may include the RF coils 20 as shown in FIG. 1 in addition to the WB coil 12. Each of the RF coils 20 is a coil placed close to the body surface of the object. There are various types for the RF coils 20. For example, as the types of the RF coils 20, as shown in FIG. 1, there are a body coil attached to the chest, abdomen, or legs of the object and a spine coil attached to the back side of the object. As another type of the RF coils 20, for example, there is a head coil for imaging the head of the object. Although most of the RF coils 20 are coils dedicated for reception, some of the RF coils 20 such as the head coil are a type that performs both transmission and reception. The RF coils 20 are configured to be attachable to and detachable from the table 51 via a cable.

The RF transmitter 33 generates each RF pulse on the basis of an instruction from the sequence controller 34. The generated RF pulse is transmitted to the WB coil 12 and applied to the object. An MR signal is generated from the object by the application of one or plural RF pulses. Each MR signal is received by the RF coils 20 or the WB coil 12.

The MR signals received by the RF coils 20 are transmitted to the coil selection circuit 36 via cables provided on the table 51 and the bed body 50. The MR signals received by the WB coil 12 are also transmitted to the coil selection circuit 36

The coil selection circuit 36 selects MR signals outputted from each RF coil 20 or MR signals outputted from the WB coil depending on a control signal outputted from the sequence controller 34 or the console 400.

The selected MR signals are outputted to the RF receiver 32. The RF receiver 32 performs analog to digital (AD) conversion on the MR signals, and outputs the converted signals to the sequence controller 34. The digitized MR signals are referred to as raw data in some cases. The AD conversion may be performed inside each RF coil 20 or inside the coil selection circuit 36.

The sequence controller 34 performs a scan of the object by driving the gradient coil power supplies 31, the RF transmitter 33, and the RF receiver 32 under the control of the console 400. When the sequence controller 34 receives raw data from the RF receiver 32 by performing the scan, the sequence controller 34 transmits the received raw data to the console 400.

The sequence controller 34 includes processing circuitry (not shown). This processing circuitry is configured as, for example, a processor for executing predetermined programs or configured as hardware such as a field programmable gate array (FPGA) or an application specific integrated circuit (ASIC).

The console 400 includes the memory 41, the display 42, the input interface 43, and the processing circuitry 40 as described above.

The memory 41 is a recording medium including a read-only memory (ROM) and a random access memory (RAM) in addition to an external memory device such as a hard disk drive (HDD) and an optical disc device. The memory 41 stores various programs executed by a processor of the processing circuitry 40 as well as various types of data and information.

The input interface 43 includes various devices for an operator to input various types of information and data, and is configured of a mouse, a keyboard, a trackball, and/or a touch panel, for example.

The display 42 is a display device such as a liquid crystal display panel, a plasma display panel, and an organic EL panel.

The processing circuitry 40 is a circuit equipped with a central processing unit (CPU) and/or a special-purpose or general-purpose processor, for example. The processor implements various functions described below by executing the programs stored in the memory 41. The processing circuitry 40 may be configured as hardware such as an FPGA and an ASIC. The various functions described below can also be implemented by such hardware. Additionally, the processing circuitry 40 can implement the various functions by combining hardware processing and software processing based on its processor and programs.

Figure 2B:
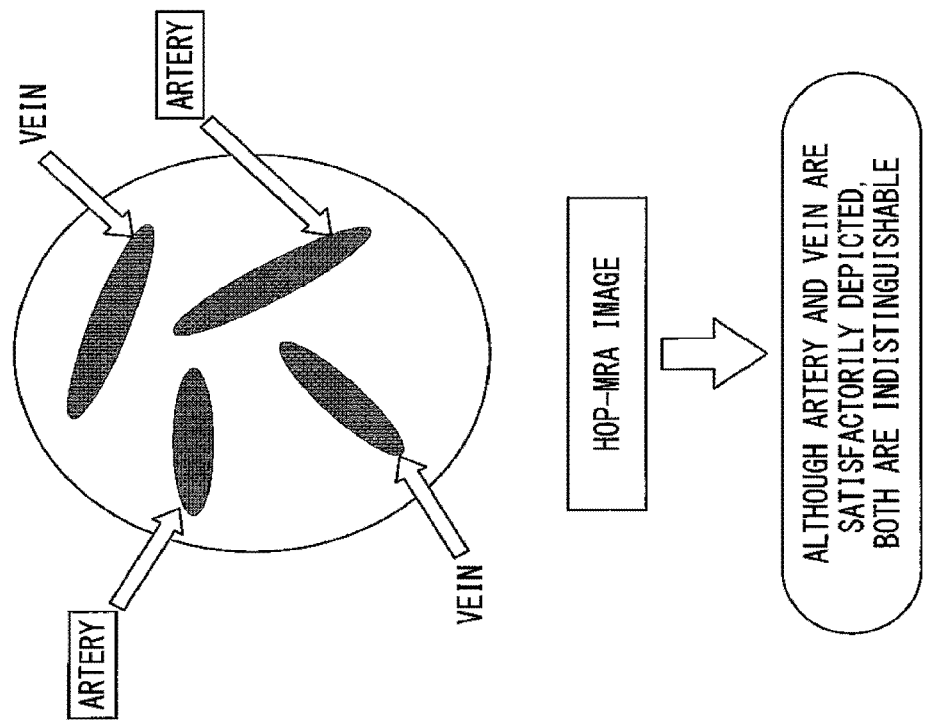
FIG. 2A and FIG. 2B are schematic diagrams illustrating the problems to be solved by the MRI apparatus according to the first and second embodiments.
Figure 2A:
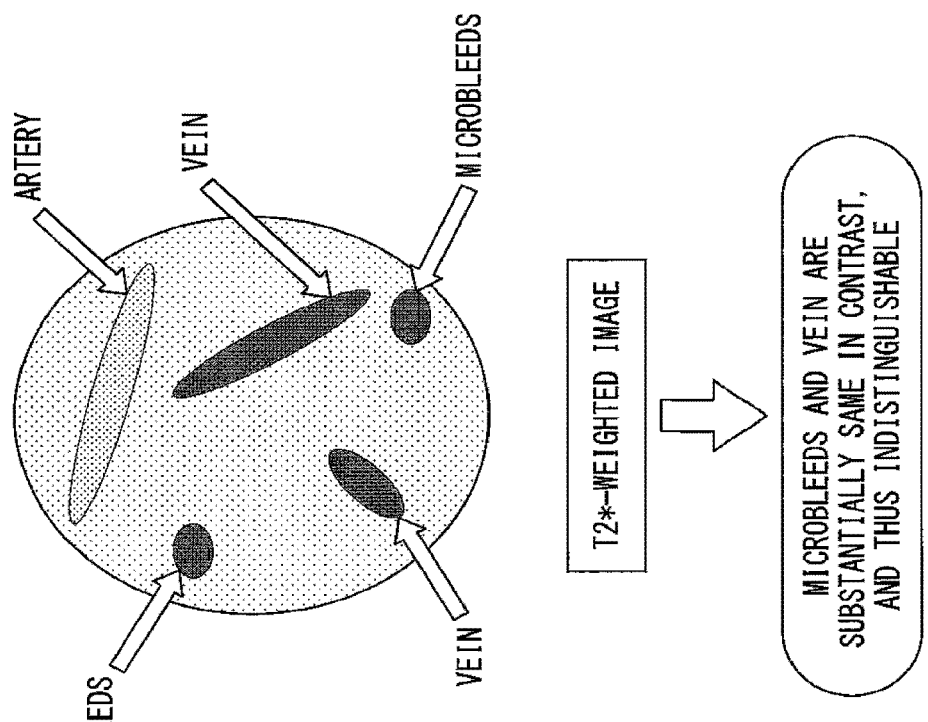

FIG. 2A and FIG. 2B are schematic diagrams illustrating the problems to be solved by the MRI apparatus 1 according to the first and second embodiments. FIG. 2A is a schematic diagram mainly illustrating the problem to be solved by the MRI apparatus 1 of the first embodiment, and FIG. 2B is a schematic diagram mainly illustrating the problem to be solved by the MRI apparatus 1 of the second embodiment.

As illustrated in FIG. 2A, in T2*-weighted images, it is known that veins and microbleeds are depicted as low signals having almost the same intensity. Microbleeds or cerebral microbleeds (CMBs) are symptoms different from cerebral hemorrhage and refer to a phenomenon that a small amount of erythrocytes (i.e., red blood cells) extravasate from broken capillaries. It is said that microbleeds may be observed as a dotted low-signal region on a T2*-weighted image.

Both of microbleeds and veins have a short T2* (Note T2* indicates an apparent transverse relaxation time), and thus are depicted as low signals having almost the same intensity with almost the same contrast in a T2*-weighted image. This makes it difficult to distinguish between microbleeds and veins in a T2*-weighted image. Meanwhile, the signal strength of arteries depicted in a T2*-weighted image is not so weak as compared with the signal strength of microbleeds or veins, so arteries are distinguishable from microbleeds or veins. Thus, for an image in which microbleeds and veins are indistinguishable, as exemplified by a T2*-weighted image, there is a strong demand for a technique to distinguish between microbleeds and veins.

On the other hand, FIG. 2B shows that both arteries and veins are satisfactorily depicted with high contrast with respect to the stationary background by a HOP-MRA (Hybrid of OPposite-contrast Magnetic Resonance Angiography) image described below. However, in the HOP-MRA image, it is difficult to distinguish between arteries and veins, and there is a demand for a technique to distinguish between both.

First Embodiment

As described above, the MRI apparatus 1 according to the first embodiment makes it possible to distinguish between microbleeds and veins. More specifically, there is almost no flow in microbleeds but there is flow in veins. Focusing on this difference in flow between microbleeds and veins, the MRI apparatus 1 distinguishes between non-flowing microbleeds and flowing blood excluding microbleeds by using phase information of MR signals. The flowing blood excluding microbleeds may include not only veins but also arteries and neovasculars.

Figure 3:
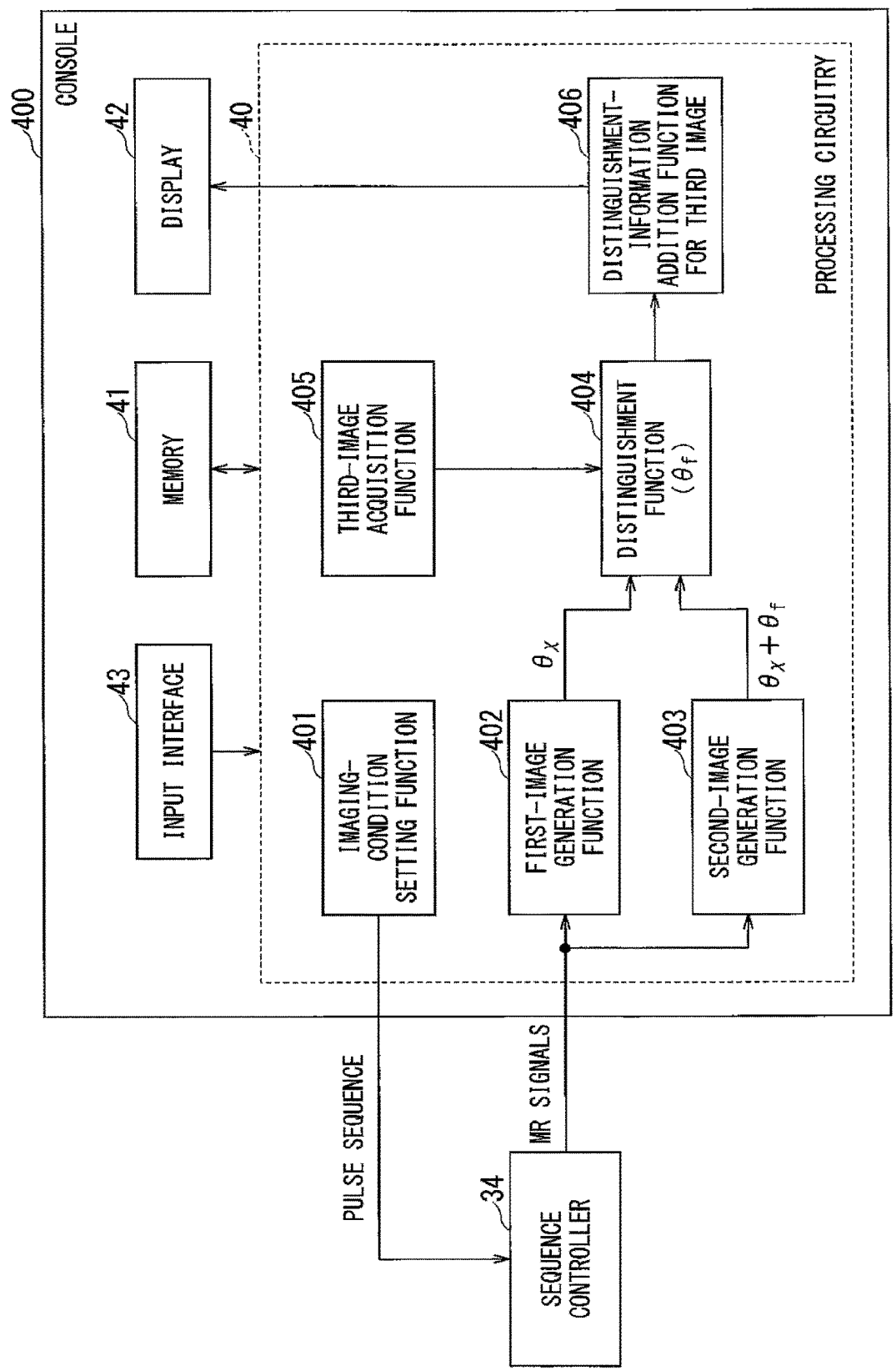
FIG. 3 is a functional block diagram of the MRI apparatus according to the first embodiment.
Figure 4:
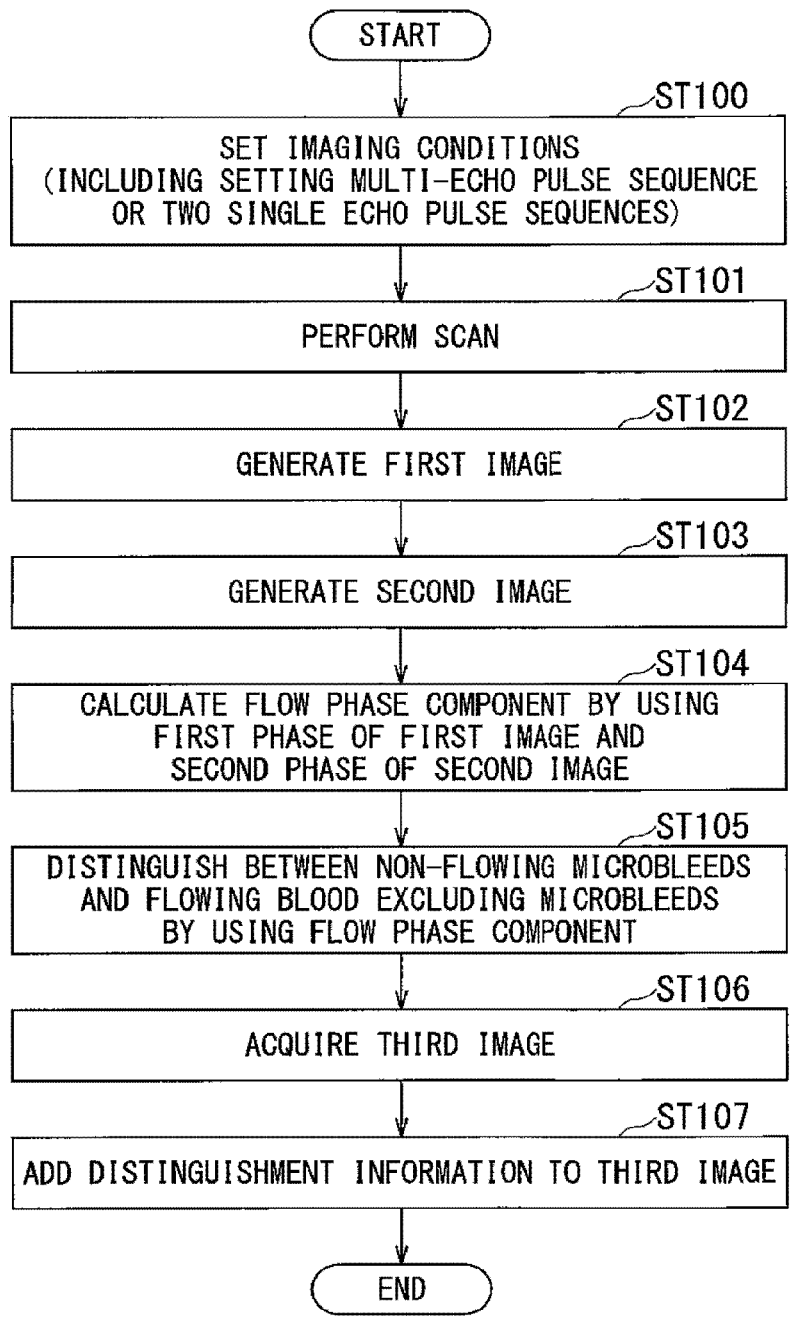
FIG. 4 is a flowchart illustrating processing performed by the MRI apparatus according to the first embodiment.

FIG. 3 is a block diagram for illustrating the functions implemented by in the MRI apparatus 1 according to the first embodiment, in particular, the functions implemented by its console 400. FIG. 4 is a flowchart illustrating the processing performed by the MRI apparatus 1 according to the first embodiment.

As shown in FIG. 3, the processing circuitry 40 of the console 400 implements an imaging-condition setting function 401, a first-image generation function 402, a second-image generation function 403, a distinguishment function 404, a third-image acquisition function 405, and a distinguishment-information addition function 406 for adding distinguishment information to a third image. The processing circuitry 40 implements each of these functions by causing the processor included in the processing circuitry 40 to execute predetermined programs stored in the memory 41.

The first-image generation function 402 generates a first image that has a first phase affected by susceptibility. The second-image generation function 403 generates a second image that has a second phase affected by both of susceptibility and flow. The distinguishment function 404 applies processing using the first phase and the second phase to the third image, in which non-flowing microbleeds and flowing blood excluding microbleeds are depicted, so as to distinguish between the non-flowing microbleeds and the flowing blood excluding microbleeds. Additionally or alternatively, the distinguishment function 404 may apply processing using a value calculated from the first phase and a value calculated from the second phase to the third image so as to distinguish between the non-flowing microbleeds and the flowing blood excluding microbleeds. The above-described "phase affected by susceptibility" refers to a phase that exhibits different values depending on the spatial distribution of the susceptibility of the object or depending on the temporal variation of the susceptibility. The "phase affected by flow" refers to a phase that exhibits different values depending on the presence/absence of flow of fluid such as blood in the object, the magnitude of flow velocity, or the direction of the flow. Note that each phase may be a phase of a complex value of a MR signal before reconstruction of the first image, or may be a phase of a complex value of a pixel of the first image.

Each function of the console 400 in FIG. 3 will be described in more detail according to the flowchart of FIG. 4.

The step ST100 in FIG. 4 corresponds to the imaging-condition setting function 401. In the step ST100, the processing circuitry 40 receives imaging conditions input from the user, and sets the imaging conditions to the sequence controller 34. The imaging conditions to be set include a multi-echo pulse sequence or two single-echo pulse sequences, for generating a first image and a second image. Hereinafter, these pulse sequences will be described.

Figure 5:
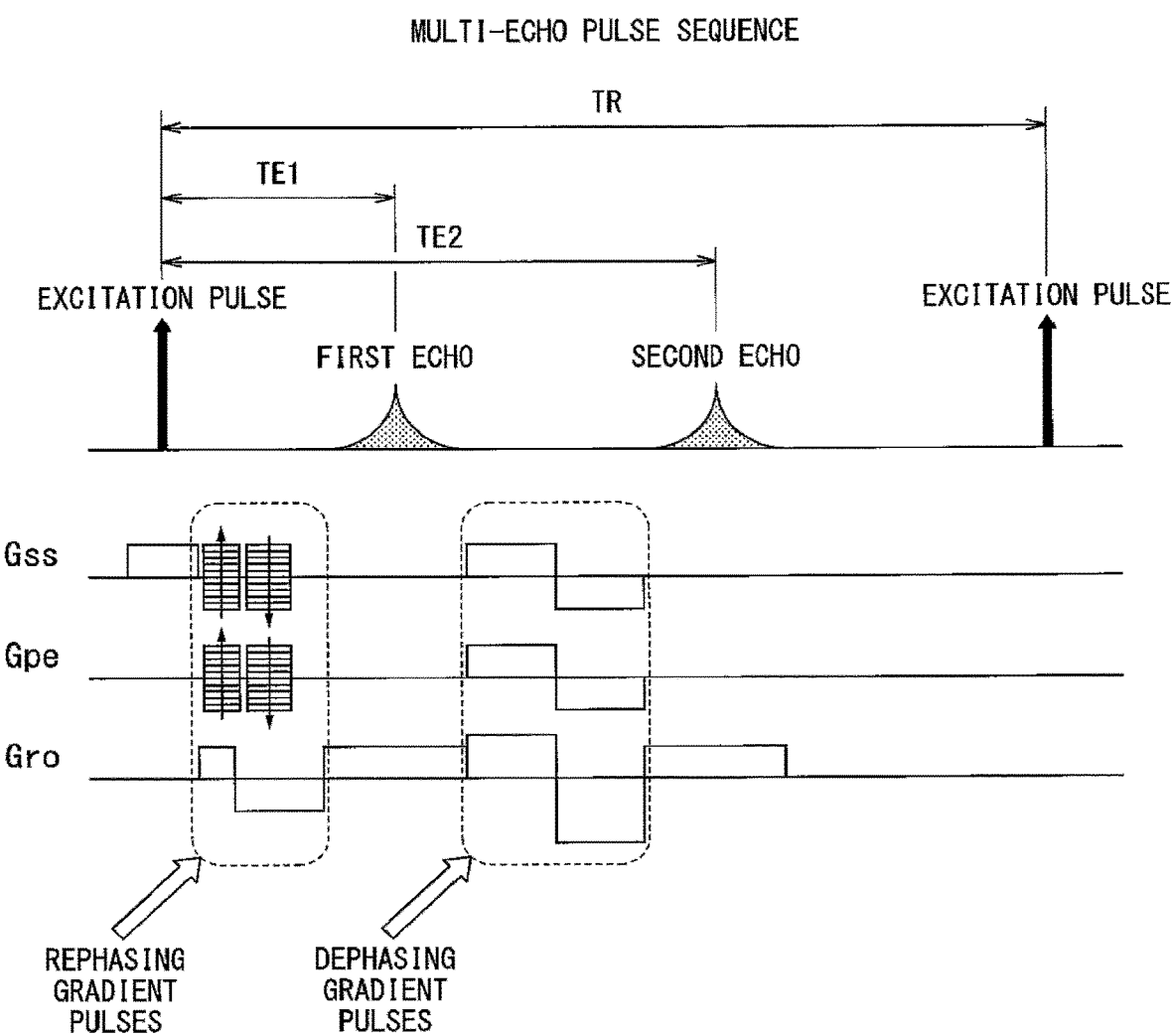
FIG. 5 is a timing chart illustrating the first pulse sequence to be used by the MRI apparatus of each embodiment.

FIG. 5 is a timing chart illustrating an example of a multi-echo pulse sequence used in the first embodiment. This multi-echo pulse sequence is a Gradient Echo (GRE) type pulse sequence, in which plural echoes are acquired from transverse magnetization generated by one excitation pulse. As shown in the upper part of FIG. 5, in the multi-echo pulse sequence, one excitation pulse is applied, then the first echo for generating the first image is acquired, and then the second echo for generating the second image is acquired. The lower part of FIG. 5 shows the gradient pulse Gss in the slice encoding direction, the gradient pulse Gpe in the phase encoding direction, and the gradient pulse Gro in the readout direction.

The first image is generated from data of the first echoes acquired in a first echo acquisition part. The first echo acquisition part includes a part for applying the rephasing gradient pulses surrounded by the left broken-line box in FIG. 5 and a part of the first echo being read out by the readout gradient pulse Gro following the rephasing gradient pulses.

On the other hand, the second image is generated from the data of the second echoes acquired in a second echo acquisition part. In FIG. 5, the second echo acquisition part includes a part for applying the dephasing gradient pulses surrounded by the right broken-line box after the first echo and a part of the second echo being read out by the readout gradient pulse Gro following the dephasing gradient pulses.

First, a description will be given of the rephasing gradient pulse. The rephasing gradient pulse is applied for suppressing phase change or phase deviation (i.e., phase shift and phase dispersion) due to flow. The rephasing gradient pulse may be referred to as a flow compensation gradient pulse in some cases.

When the slice encoding gradient pulse Gss or the phase encoding gradient pulse Gpe is applied, a flowing tissue such as arterial blood or venous blood has a phase deviation (i.e., phase error) with respect to the phase value corresponding to the slice encoding amount or phase encoding amount having been set for stationary tissues. The phase deviation varies depending on the flow rate. By applying the rephasing gradient pulse in the slice encoding direction or the phase encoding direction, the phase deviation due to the flow is canceled, while the same slice encoding amount and phase encoding amount as the stationary tissues can be obtained, even though the tissue is flowing or moving.

When the readout gradient pulse is applied to flowing tissues such as arterial blood or venous blood, those flowing tissues are subjected to phase deviation due to the flow rate, and thus the phase at the center position of the readout gradient pulse does not become zero, which causes a shift in peak position of the echo and a decrease in peak value. The rephasing gradient pulse in the readout direction is applied to cope with this issue. By applying the rephasing gradient pulse in the readout direction, an echo peak is formed at the center position of the readout gradient pulse and the peak value is maintained similarly to the stationary tissues, while the phase deviation due to the flow is canceled.

On the other hand, the dephasing gradient pulse is applied for enhancing the phase change due to flow (i.e., phase shift and phase deviation due to the flow). The shape of the dephasing gradient pulse is, for example, a bipolar type in which the area on the positive side and the area on the negative side are equal. Even when the dephasing gradient pulse is applied, the phase of the stationary tissues does not change. Conversely, when the dephasing gradient pulse is applied to flowing tissues such as arterial blood or venous blood, phase change occurs depending on the flow rate.

When the dephasing gradient pulse is applied, MR signals from arterial blood and venous blood become low signals due to dephasing (i.e., those MR signals are depicted as Black Blood after reconstruction). For this reason, as in the second echo acquisition part, an imaging method with application of dephasing gradient pulses is sometimes referred to as a flow-sensitive black blood (FSBB) method.

Returning to FIG. 4, in the step ST101, the scanner executes a scan on the basis of the multi-echo pulse sequence and the other imaging conditions that have been set in the step ST100.

In the multi-echo pulse sequence shown in FIG. 5, the scanner acquires the first and second echoes while changing at least one of the slice encoding amount and the phase encoding amount at intervals of excitation pulses, i.e., for each repetition period TR. The first echo is acquired when the first echo time TE1 elapses from the application timing of the excitation pulse, and the second echo is acquired when the second echo time TE2 elapses from the application timing of the excitation pulse. The above-described sequence is for the case of generating a three-dimensional image. In the case of generating a two-dimensional image, it is achieved by changing only the phase encoding amount from the above-described sequence.

When first echoes (i.e., the first echo group) are acquired by the slice encoding number and phase encoding number necessary for generating the first image and second echoes (i.e., the second echo group) are acquired by the slice encoding number and phase encoding number necessary for generating the second image, the scan in the step ST101 is completed.

In the next step ST102, the first image is generated by using the data of the acquired first echo group. In the next step ST103, the second image is generated by using the data of the acquired second echo group. Generation of the first image is implemented by the first-image generation function 402 shown in FIG. 3, and generation of the second image is implemented by the second-image generation function 403. The order of the step ST102 and the step ST103 may be reversed.

The first image is an image obtained by reconstructing the data of the first echo group by computation such as inverse Fourier transform, and the value of each pixel of the first image is a complex number. The phase $\theta_1(r)$ of each pixel of the first image is expressed by the following equation (1).

$$\theta_1(r)=\tan^{-1}(\text{Im}(r)/R(r)) \quad \text{Equation (1)}$$

In Equation (1), each pixel position is defined as "r", the real part of the pixel value at the pixel position r is defined as R(r), and the imaginary part of the pixel value at the pixel position r is defined as Im(r).

The first-image generation function 402 generates the first image and calculates the phase $\theta_1(r)$ (i.e., the first phase) for each pixel of the first image by using Equation (1) in the step ST102. Then, the calculated phase $\theta_1(r)$ for each pixel of the first image is sent to the distinguishment function 404.

Note that it is assumed that phase $\theta_0(r)$ due to non-uniformity of the static magnetic field and the RF magnetic field, or due to imperfection of the MRI apparatus 1 including the eddy-current magnetic field is completely corrected. Under this assumption, in general, it can be considered that the phase of each pixel of non-flowing tissues in the reconstructed image becomes the phase $\theta\chi(r)$ due to the susceptibility $\chi$ of the object tissue. Meanwhile, under this assumption, in general, it can be considered that the phase of each pixel of flowing tissues such as a blood vessel in the reconstructed image becomes the sum of the phase $\theta\chi(r)$ due to the susceptibility $\chi$ and the phase $\theta f(r)$ due to the flow (i.e., flow phase component).

Since rephasing gradient pulses are used to acquire the data of the first echo group as described above, the flow phase component $\theta f(r)$ due to the flow can be suppressed to almost zero. Consequently, $\theta_1(r)$ in the first image can be expressed only by the phase $\theta\chi_1(r)$ due to the susceptibility $\chi$ as in the following equation (2), not only for pixels in a non-flowing tissue such as a stationary tissue and microbleeds but also for pixels in a flowing tissue such as a vein and an artery and each pixel.

$$\theta_1(r)=\theta\chi_1(r) \quad \text{Equation (2)}$$

The second image is an image obtained by reconstructing the data of the second echo group by calculation including inverse Fourier transform and the value of each pixel of the second image is a complex number, similarly to the first image. The phase $\theta_2(r)$ of each pixel of the second image can be calculated from the real part R(r) and the imaginary part of the pixel value at each pixel position r, similarly to the first image.

The second-image generation function 403 generates the second image and calculates the phase $\theta_2(r)$ (i.e., the second phase) for each pixel of the second image on the basis of the calculation similar to the equation (1) in the step ST103 to output the calculation result to the distinguishment function 404.

Since dephasing gradient pulses are used for acquiring the data of the second echo group, in each pixel of flowing tissues such as veins and arteries, the flow phase component $\theta f(r)$ due to the flow is not suppressed to zero but rather shows a large non-zero value. As a result, for each pixel of flowing tissues such as veins and arteries, the phase $\theta_2(r)$ in the second image can be expressed as the sum of the phase $\theta\chi_2(r)$ due to the susceptibility $\chi$ and the flow phase component $\theta f_2(r)$ due to the flow as in the following equation (3).

$$\theta_2(r)=\theta\chi_2(r)+\theta f_2(r) \quad \text{Equation (3)}$$

Thus, the flow phase component $\theta f_2(r)$ due to the flow in the second image can be expressed by the following equation (4).

$$\theta f_2(r)=\theta_2(r)-\theta\chi_2(r) \quad \text{Equation (4)}$$

That is, when the phase $\theta\chi_2(r)$ due to the susceptibility $\chi$ in the second image is determined, the value of the phase $\theta f_2(r)$ due to the flow in the second image can determined by the difference between the phase $\theta\chi_2(r)$ and the phase $\theta_2(r)$ measured from the second image.

The phase $\theta\chi(r)$ due to the susceptibility $\chi$ can be expressed by the following equation (5) by using the echo time TE, a constant (gyromagnetic ratio) $\gamma$, and the spatial variation $\Delta B\chi(r)$ of the static magnetic field due to the spatial variation $\Delta\chi(r)$ of the susceptibility $\chi$.

$$\theta\chi(r)=-\gamma\cdot\Delta B\chi(r)\cdot TE \quad \text{Equation (5)}$$

Between corresponding pixels at the same position of the first image and the second image, it can be considered that the spatial variation $\Delta\chi(r)$ of the susceptibility $\chi$ is the same, and thus the spatial variation $\Delta B\chi(r)$ of the static magnetic field is also the same. Since the echo time of the first echo corresponding to the first image is TE1 and the echo time of the second echo corresponding to the second image is TE2, the phase $\theta\chi_1(r)$ due to the susceptibility in the first image is expressed by the following equation (6) and the phase $\theta\chi_2(r)$ due to the susceptibility in the second image is expressed by the following equation (7).

$$\theta\chi_1(r) = -\gamma \cdot \Delta B\chi(r) \cdot TE1 \qquad \text{Equation (6)}$$

$$\theta\chi_2(r) = -\gamma \cdot \Delta B\chi(r) \cdot TE2 \qquad \text{Equation (7)}$$

The following equation (8) is obtained from the equations (6), (7), and (2).

$$\theta\chi_2(r) = \theta\chi_1(r) \cdot \{(TE2)/(TE1)\} = \theta_1(r) \cdot \{(TE2)/(TE1)\} \qquad \text{Equation (8)}$$

The equation (8) means that the phase $\theta\chi_2(r)$ due to the susceptibility $\chi$ in the second image can be calculated or estimated from the known first echo time TE1, the known second echo time TE2, and the first phase $\theta_1(r)$ determined from the first image.

In the step ST104 of FIG. 4, the phase $\theta\chi_2(r)$ due to the susceptibility $\chi$ in the second image is determined (estimated) on the basis of the equation (8) by using the first phase $\theta_1(r)$ calculated in the step ST102 and both of the first echo time TE1 and the second echo time TE2, which have been set as the imaging conditions. In the step ST104, the flow phase component $\theta f_2(r)$ in the second image is further calculated on the basis of the equation (4) by using the estimated phase $\theta\chi_2(r)$ due to the susceptibility $\chi$ in the second image and the second phase $\theta_2(r)$ calculated in the step ST103.

In the next step ST105, distinguishment between pixels of flowing tissues and pixels of non-flowing tissues is performed by using the value of the calculated flow phase component $\theta f_2(r)$. For example, distinguishment between non-flowing microbleeds and flowing blood excluding microbleeds such as veins and arteries is performed. Specifically, when the value of the flow phase component $\theta f_2(r)$ is smaller than a predetermined threshold value (for example, zero) for the target pixel, the target pixel is determined to belong to non-flowing microbleeds. When the value of the flow phase component $\theta f_2(r)$ is equal to or larger than the predetermined threshold value for the target pixel, the target pixel is determined to belong to flowing blood excluding microbleeds.

The processing of the steps ST104 and ST105 is performed by the distinguishment function 404 in FIG. 3.

In the next step ST106, the third-image acquisition function 405 acquires the third image from, for example, the memory 41 and/or the outside of the MRI apparatus 1. The third image is an image in which veins and microbleeds are indistinguishable by contrast of the image, such as a T2*-weighted image and a quantitative susceptibility mapping (QSM) image described below. The third image may be an image generated by the MRI apparatus 1 including the above-described first image and second image or may be an MR image generated by another MRI apparatus other than the MRI apparatus 1. Additionally or alternatively, the third image may be a CT image generated by a computed tomography (CT) apparatus.

In the step ST107, after performing positioning, or registration, between the acquired third image and the second image as necessary, information on the presence/absence of flow distinguished in the step ST105 is added to the third image. Since information on the presence/absence of flow is added to the third image in which neither veins nor microbleeds are made distinguishable, both can be distinguished from each other in such a manner that each pixel indicative of presence of flow is regarded as a pixel belonging to a vein and each pixel indicative of absence of flow is regarded as a pixel belonging to microbleeds. The processing of the step S107 is performed by the distinguishment-information addition function 406 for the third image.

The third image to which the distinguishment information is added is displayed on the display 42 of the MRI apparatus 1, for example.

Figure 6:
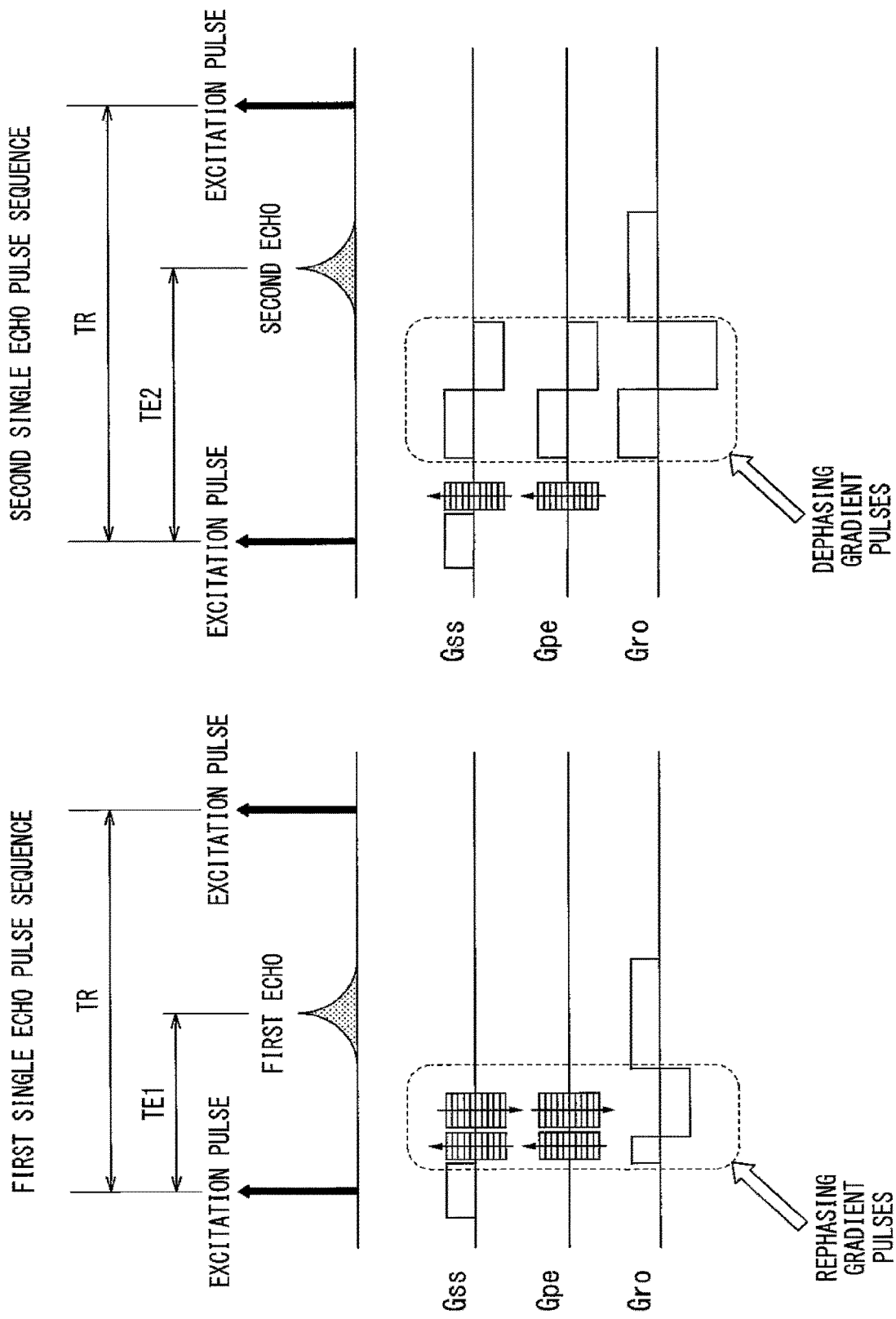
FIG. 6A and FIG. 6B are timing charts illustrating the second pulse sequence to be used by the MRI apparatus of each embodiment.

Although the multi-echo pulse sequence for acquiring two types of echoes including each first echo and each second echo is used in the first embodiment, the pulse sequence used in the first embodiment is not limited to the multi-echo pulse sequence. FIG. 6A and FIG. 6B illustrate two single echo pulse sequences (i.e., first single echo pulse sequence and second single echo pulse sequence) that can be used in the first embodiment.

FIG. 6A is a timing chart of the first single echo pulse sequence for acquiring the first echoes, and one first echo is acquired by applying one excitation pulse in the first single echo pulse sequence. The first single echo pulse sequence corresponds to the first echo acquisition part in the multi-echo pulse sequence described above, and the rephasing gradient pulse is applied between the excitation pulse and the first echo acquisition period.

FIG. 6B is a timing chart of the second single echo pulse sequence for acquiring the second echoes, and one second echo is acquired by applying one excitation pulse in the second single echo pulse sequence. The second single echo pulse sequence corresponds to the second echo acquisition part in the multi-echo pulse sequence described above, and the dephasing gradient pulse is applied between the excitation pulse and the second echo acquisition period.

In the step ST100 of FIG. 4, the two single echo pulse sequences shown in FIG. 6A and FIG. 6B are set. In the next step ST101, a scan based on the respective single echo pulse sequences is performed. In the next step ST102, the first image is generated from the first echo group acquired by the first single echo pulse sequence, and in the next step ST103, the second image is generated from the second echo group acquired by the second single echo pulse sequence.

The processing from the steps ST105 to ST107 is the same as the processing in the multi-echo pulse sequence described above, and duplicate description is omitted.

Figure 7:
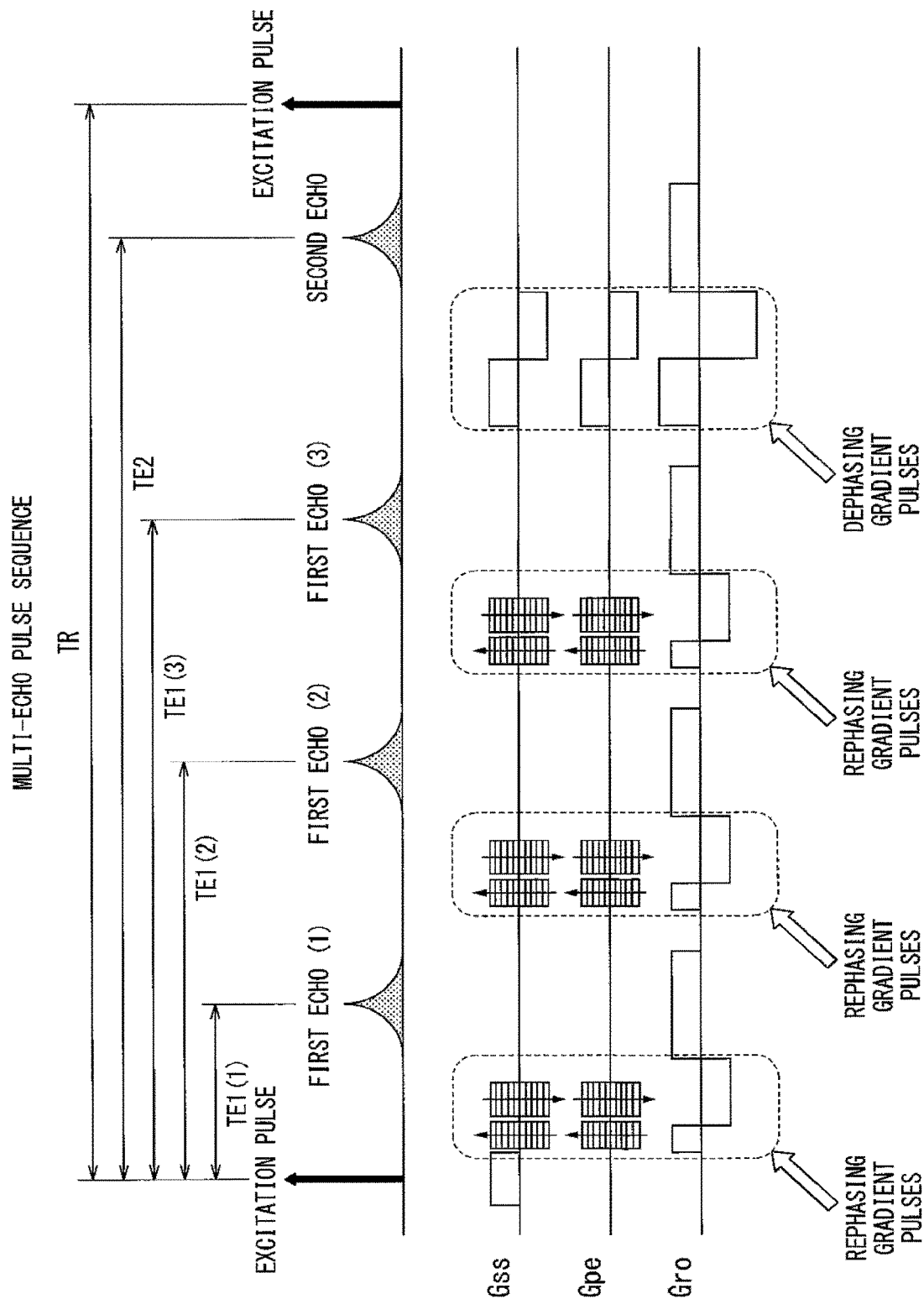
FIG. 7 is a timing chart illustrating the third pulse sequence to be used by the MRI apparatus of each embodiment.

FIG. 7 is a timing chart illustrating another multi-echo pulse sequence to be set in the step ST100 of FIG. 1. The multi-echo pulse sequence shown in FIG. 7 includes plural (three in the case of FIG. 7) first echo acquisition parts, in each of which the rephasing gradient pulses are applied.

In the step ST102 of FIG. 4, three first images corresponding to the respective three echo times TE1(1), TE1(2), and TE1(3) are generated in the three first echo acquisition parts. In the step ST102, the phase $\theta_1(r)$ is calculated for each of the three first images on the basis of the equation $\theta_1(r) = \theta\chi_1(r)$.

Since plural (for example, three) phases $\theta\chi_1(r)$ of the respective first images are obtained, estimation accuracy of the susceptibility $\theta\chi_2(r)$ of the second image can be improved by the curve fitting method or the averaging method. As a result, estimation accuracy of the flow phase component $\theta f_2(r)$ of the second image is improved, which improves reliability of the distinguishment processing between non-flowing microbleeds and flowing blood excluding microbleeds in the step ST105.

Modification of First Embodiment

Figure 8:
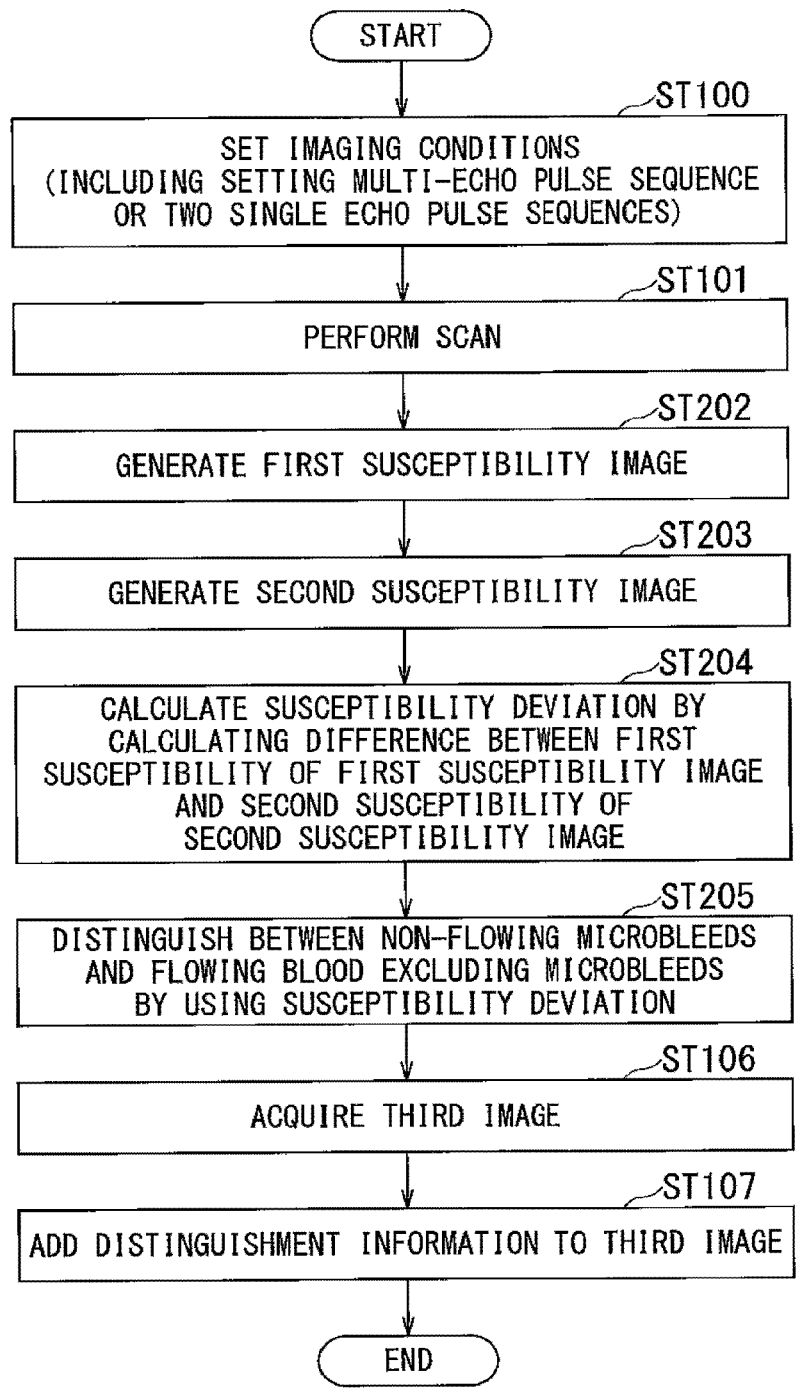
FIG. 8 is a flowchart illustrating processing performed by the MRI apparatus according to a modification of the first embodiment.

FIG. 8 is a flowchart illustrating processing performed by the MRI apparatus 1 according to a modification of the first embodiment.

The multi-echo pulse sequence or two single-echo pulse sequences to be set in the step ST100 are the same as those in the first embodiment described above. The execution of the scan in the step ST101 is also the same as that in the first embodiment.

In the scan performed in the step ST101, the data of the first echo group are acquired with application of the rephasing gradient pulses and the data of the second echo group are acquired with application the dephasing gradient pulses.

In the step ST202, the first susceptibility image is generated by using the data of the first echo group. A susceptibility image is a map obtained by quantitatively calculating susceptibility $\chi$ for each pixel and arraying the calculated susceptibility $\chi$ as the pixel value of each pixel, and is also called QSM (Quantitative Susceptibility Mapping). The susceptibility image is generated in the following manner. First, a phase component of the pixel is calculated from the complex image generated by reconstructing the data of the first echo group, then a phase image is generated from the calculated phase component of the pixel, and then susceptibility $\chi$ of the pixel is calculated by, for example, performing the processing described in JP 2017-70386 A on the phase image.

Since the rephasing gradient pulses are used for acquiring the first echo group, in the complex image generated by reconstructing the data of the first echo group, the flow phase component $\theta f(r)$ due to the flow is suppressed to almost zero. Thus, the phase $\theta_1(r)$ in this complex image (which corresponds to the above-described first image) can be expressed only by the phase $\theta\chi_1(r)$ due to the susceptibility $\chi$ for both types of pixel including the pixel in a flowing tissue such as a vein and an artery and the pixel in a non-flowing tissue such as a stationary tissue and microbleeds. Hence, the value of the susceptibility $\chi$ in the first susceptibility image generated from the data of the first echo group is less affected by the phase change due to the flow and indicates a correct value not only for the pixel in a non-flowing tissue such as a stationary tissue and microbleeds but also for the pixel of a flowing tissue such as a vein and an artery.

In the step ST203, the second susceptibility image is generated by using the data of the second echo group. Since the dephasing gradient pulses are used for acquiring the second echo group, in the complex image generated from the data of the second echo group (which corresponds to the above-described second image), the phase $\theta_2(r)$ in the pixel indicative of absence of flow such as a stationary tissue or microbleeds are expressed only by the phase $\theta\chi_2(r)$ due to the susceptibility x. For the same reason, in the complex image generated from the data of the second echo group, the phase $\theta_2(r)$ in the pixel indicative of presence of flow such as a vein and an artery can be expressed as the sum of the phase $\theta\chi_2(r)$ due to the susceptibility $\chi$ and the flow phase component $\theta f_2(r)$ due to the flow as indicated by the equation (3).

Thus, for the pixel in a non-flowing tissue such as microbleeds and a stationary tissue, the value of the susceptibility $\chi$ in the second susceptibility image generated from the data of the second echo group indicates the correct value and becomes equal to the value of the susceptibility $\chi$ in the first susceptibility image. However, for the pixel in a flowing tissue such as a vein and an artery, the value of the susceptibility $\chi$ in the second susceptibility image does not match the value of the susceptibility $\chi$ in the first susceptibility image.

Accordingly, in the step ST204, the susceptibility deviation is calculated for each pixel by calculating difference between the susceptibility of the first susceptibility image (i.e., first susceptibility) and the susceptibility of the second susceptibility image (i.e., second susceptibility) for each pixel.

In the step ST205, the susceptibility deviation is used for distinguishing between non-flowing microbleeds and flowing blood excluding microbleeds. Specifically, a pixel with susceptibility deviation smaller than a predetermined threshold value is determined as a pixel belonging to non-flowing microbleeds, while a pixel with susceptibility deviation equal to or larger than the threshold value is determined as a pixel belonging to flowing blood (for example, a vein) excluding microbleeds.

As described above, in a T2*-weighted image, veins and microbleeds are depicted as low signals having almost the same intensity and thus are indistinguishable from each other. Also in a susceptibility image (QSM), veins and microbleeds are almost the same in terms of susceptibility and thus it is said to be difficult to distinguish between both. By contrast, according to the first embodiment and the modification of the first embodiment, it is possible to distinguish between non-flowing microbleeds and flowing blood (for example, a vein) excluding microbleeds.

The image (third image) to which the distinguishment processing of the MRI apparatus 1 can be applied is not limited to the above-described T2*-weighted image and/or the susceptibility image (QSM) but includes an image in which regions having substantially the same contrast are included. Further, the target of the distinguishment processing is not limited to a region of non-flowing microbleeds and a region of flowing blood (for example, a vein) excluding microbleeds but includes a region that can be identified by distinguishing difference in flow. For example, the target of the distinguishment processing includes a region that can be identified by distinguishing presence/absence of flow, distinguishing difference in flow rate, or distinguishing difference in flow direction.

In addition, when an image as a target of the distinguishment processing includes regions of fluid or tissue having different susceptibility values, and when these regions are substantially the same in terms of contrast, these regions may be identified by distinguishing difference in susceptibility between these regions. For example, for images in which an artery and a vein are depicted with substantially the same contrast, it is possible to distinguish the region of the artery and the region of the vein by distinguishing difference in susceptibility between both as described below.

Second Embodiment

Figure 9:
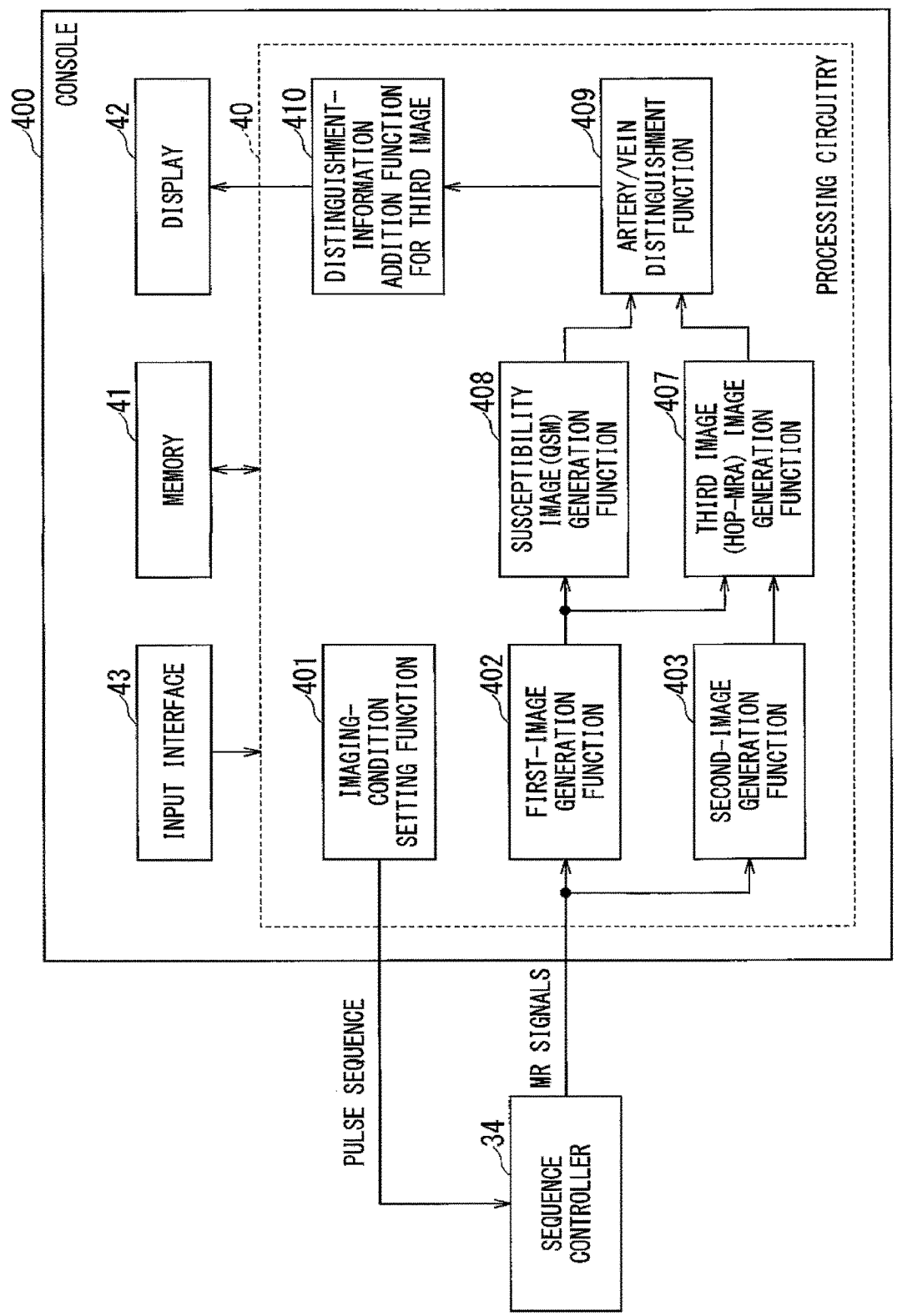
FIG. 9 is a functional block diagram of the MRI apparatus according to the second embodiment.
Figure 10:
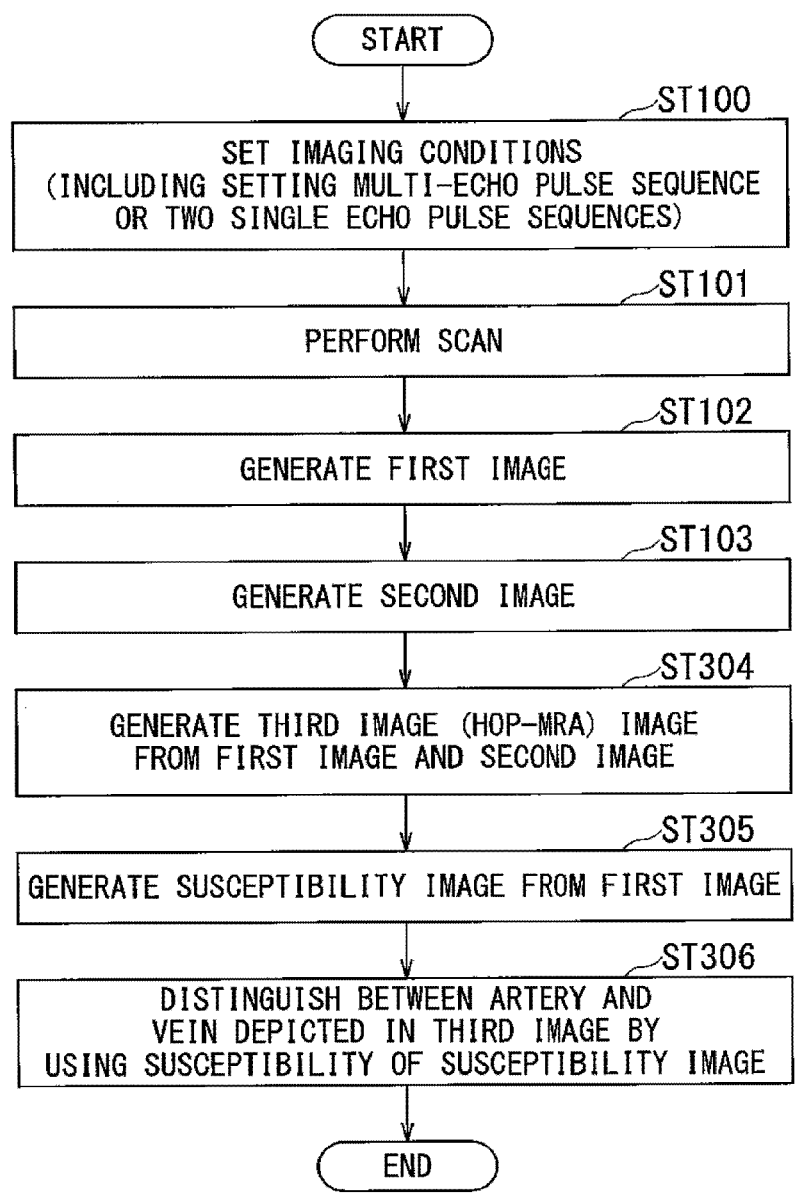
FIG. 10 is a flowchart illustrating processing performed by the MRI apparatus according to the second embodiment.

FIG. 9 is a block diagram illustrating the functions implemented by in the MRI apparatus 1 according to the second embodiment, in particular, the functions implemented by its console 400. FIG. 10 is a flowchart illustrating the processing performed by the MRI apparatus 1 according to the second embodiment.

As shown in FIG. 9, the MRI apparatus 1 according to the second embodiment newly includes functions 407 to 410, instead of the distinguishment function 404, the third-image acquisition function 405, and the distinguishment-information addition function 406 for the third image in the first embodiment. The MRI apparatus 1 according to the second embodiment includes the third image (HOP-MRA) image generation function 407, the susceptibility image (QSM) generation function 408, the artery/vein distinguishment function 409, and the distinguishment information addition function 410 for adding distinguishment information to the third image. The processing circuitry 40 implements each of these functions by causing the processor included in the processing circuitry 40 to execute predetermined programs stored in the memory 41.

The third image (HOP-MRA) generation function 407 generates the third image (for example, a HOP-MRA image described below), in which both arteries and veins are depicted with high contrast with respect to a stationary background, by using the first image and the second image that are generated in a manner similar to the first embodiment.

The susceptibility image (QSM) generation function 408 generates a susceptibility image (QSM) from the first image.

The artery/vein distinguishment function 409 distinguishes between arteries and veins for the third image such as a HOP-MRA image by using the value of the susceptibility of each pixel of the generated susceptibility image or by using the value of the first phase of the first image.

The distinguishment-information addition function 410 adds distinguishment information to the third image. The distinguishment information is information for distinguishing between arteries and veins that are depicted in the third image such as the HOP-MRA image. The distinguishment information may include, for example, color, density, or characters.

Each function of the console 400 in FIG. 9 will be described in more detail according to the flowchart of FIG. 10. The processing from the steps ST100 to ST103 is the same as in the first embodiment (FIG. 4) and duplicate description is omitted.

In the step ST304, a HOP-MRA (Hybrid of OPposite-contrast Magnetic Resonance Angiography) image is generated as the third image from the first image and the second image. FIG. 11A to FIG. 11C are schematic diagrams illustrating the concept of generating the HOP-MRA image.

FIG. 11A is a schematic diagram of the first image and illustrates the signal intensity $S_W$ of regions of the respective blood vessels A, B, and C, which are arranged in the Z-axis direction and different in thicknesses from each other. This first image is an image generated from the data of the first echo group that is acquired by applying the rephasing gradient pulses in FIG. 5 to FIG. 7. The first echo acquisition part for acquiring the data of the first echo group is a pulse sequence corresponding to a TOF (Time of Flight) method, for example.

The TOF method is an imaging method based on the inflow effect. When excitation is repeatedly performed with repetitive time TR shorter than the longitudinal relaxation time T1, unsaturated spin of blood inflowing from outside the excited region has a higher signal than that of the saturated stationary spin in the excited region, and this is the inflow effect. In the TOF method, fast blood flow of an artery is depicted with high signal (WB: White Blood) with respect to background tissues. However, the TOF method is not suitable for depicting slow blood flow such as a venous system and peripheral arteries, which are distant from the inflow position toward the excitation region.

FIG. 11B is a schematic diagram of the second image and illustrates the signal intensity $S_B$ of the regions of the respective blood vessels A, B, and C, which are arranged in the Z-axis direction and different in thickness from each other, in a manner similar to FIG. 11A. The second image is an image generated from the data of the second echo group acquired by applying the dephasing gradient pulses in FIG. 5 to FIG. 7. The second echo acquisition part for acquiring the data of the second echo group corresponds to an imaging method called a Flow-Sensitive Black Blood (FSBB) method.

The FSBB method uses a pulse sequence of a GRE type. In the pulse sequence of the FSBB method, one set of dephasing gradient pulses are applied between an excitation pulse and a readout gradient pulse such that the dephasing gradient pulses disperses the blood flow signal and blood vessels of both of arteries and veins are depicted with lower signal (black blood) than background tissues.

FIG. 11C is a schematic diagram of the third image and illustrates the signal intensity $S_H$ of the regions of the respective blood vessels A, B, and C, which are arranged in the Z-axis direction and different in thickness from each other, in a manner similar to FIG. 11A and FIG. 11B. The third image (for example, the HOP-MRA image) is generated by subtracting the second image from the first image or by performing weighted subtraction of the second image from the first image. For example, when the weight is defined as α, it is calculated by $S_H=S_W-\alpha S_B$. When the second image being a Black Blood image is subtracted from the first image that is a White Blood image, in the HOP-MRA image, the contrast with respect to background tissues of both of arterial and venous blood vessels is further enhanced. Thus, both arteries and veins are satisfactorily depicted in the HOP-MRA image. However, in the HOP-MRA image, arteries and veins cannot be distinguished.

Returning to FIG. 10, in the step ST305, a susceptibility image (QSM) is generated from the first image. In the susceptibility image generated from the first image (i.e., in the first susceptibility image), the influence of the phase change due to the flow is suppressed as described above. Thus, the value of susceptibility in the first susceptibility image indicates a correct value not only for the pixel of a non-flowing microbleeds and a stationary tissue but also for the pixel of a flowing part such as veins and arteries.

In general, red blood cells contain a large amount of hemoglobin that carries oxygen, and hemoglobin exhibits diamagnetism when being bound to an oxygen molecule, and exhibits paramagnetism after releasing oxygen in capillaries (deoxyhemoglobin). For this reason, venous blood exhibits paramagnetism, and its susceptibility $\chi$ exhibits a positive value. On the other hand, arterial blood exhibits a near-zero diamagnetism and its susceptibility $\chi$ exhibits a near-zero negative value.

The microbleeds are considered to have a property close to that of a vein, exhibits paramagnetism, and its susceptibility $\chi$ has a positive value. Besides, it is known that a calcified region exhibits diamagnetism and its susceptibility $\chi$ exhibits a larger negative value than that of arterial blood.

Thus, in the step ST306 of FIG. 10, the susceptibility $\chi$ of the susceptibility image generated in the step ST305 is used for distinguishing between arteries and veins depicted in the third image (for example, the HOP-MRA image).

For example, the artery/vein distinguishment function 409 refers to the region in the susceptibility image, the region corresponding to the blood vessel (i.e., blood vessel region in which arteries and veins are not distinguished) as a target of the distinguishment processing in the third image. When the sign of the susceptibility of the blood vessel as the target of the distinguishment processing is positive and the absolute value of the susceptibility is larger than a predetermined threshold value, the blood vessel is determined to be a vein. Conversely, when the sign of the susceptibility of the blood vessel is negative and the absolute value of the susceptibility is smaller than the predetermined threshold, the blood vessel is determined to be an artery.

Instead of the above-described processing, arteries and veins may be distinguished only by the sign of the susceptibility, or arteries and veins may be distinguished only by the absolute value of the susceptibility. In the former case, the blood vessel is determined to be a vein when the sign of the susceptibility is positive, and is determined to be an artery when the sign of the susceptibility is negative (or when it is difficult to distinguish between positive and negative). In the latter case, the blood vessel is determined to be a vein when the absolute value of the susceptibility is larger than the predetermined threshold value, and is determined to be an artery when the absolute value of the susceptibility is smaller than the threshold value.

FIG. 12A shows a schematic HOP-MRA image before distinguishing between arteries and veins, and FIG. 12B shows a HOP-MRA image after distinguishing between arteries and veins. As shown in FIG. 12A and FIG. 12B, the MRI apparatus 1 of the second embodiment can distinguish between arteries and veins in the third image (for example, a HOP-MRA image) in which both arteries and veins are satisfactorily depicted.

Modification of Second Embodiment

In the second embodiment described above, arteries and veins are distinguished by using the value of the susceptibility $\chi$ of the susceptibility image generated from the first image and/or the positive/negative sign of the susceptibility $\chi$.

Instead of the above-described processing, in the modification of the second embodiment, the phase of the first image is used for distinguishing between arteries and veins without calculating the susceptibility. It is considered that the phase of the first image becomes positive or negative so as to correspond to the positive or negative value of the susceptibility $\chi$. Hence, for example, when the phase of the pixel value of the blood vessel as the target of the distinguishment processing is positive, this pixel can be determined as a pixel belonging to a vein. When the phase of the pixel value of the blood vessel is negative, this pixel can be determined as a pixel belonging to an artery.

Depending on the type of MRI apparatus, the phase of the first image may be reversed. Although the susceptibility of an artery is a negative value, the absolute value of the susceptibility $\chi$ of an artery is a small value close to zero as described above. Thus, the phase of an artery in the first image tends to have a large error. By contrast, since the absolute value of the susceptibility of a vein is a large value with respect to an artery, an error in the phase of a vein in the first image is small, and the variation in the measured values is also small.

Accordingly, for the first image, the phase of the blood vessel which is readily determined as a vein based on its anatomical position may be determined as a reference phase in advance. This reference phase may be compared with the phase of each blood vessel, which is difficult to distinguish between an artery and a vein, in such a manner that each blood vessel having a phase close to the reference phase is determined as a vein and all of the other blood vessels are determined as arteries.

According to at least one embodiment described above, in an image in which blood vessels or blood are depicted, it is possible to distinguish a state of blood and/or blood flow, for example, it is possible to distinguish between arteries and veins, or distinguish between non-flowing microbleeds and flowing blood excluding microbleeds.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An MRI apparatus comprising:
    a memory configured to store a predetermined program; and
    processing circuitry configured, by executing the predetermined program, to
        generate a first image having a first phase affected by susceptibility,
        generate a second image having a second phase affected by both of the susceptibility and flow, and
        distinguish difference in susceptibility or flow for a pixel of a third image by using the first phase and the second phase or by using a value calculated from the first phase and a value calculated from the second phase, the third image having regions which are substantially same in contrast.

2. The MRI apparatus according to claim 1, wherein the first image is generated from first data acquired by a first pulse sequence in which a rephasing gradient pulse for suppressing phase change due to the flow is applied.

3. The MRI apparatus according to claim 1, wherein the second image is generated from second data acquired by a second pulse sequence in which a dephasing gradient pulse for enhancing phase change due to the flow is applied.

4. The MRI apparatus according to claim 2,
    wherein the second image is generated from second data acquired by a second pulse sequence in which a dephasing gradient pulse for enhancing phase change due to the flow is applied.

5. The MRI apparatus according to claim 1, wherein:
    each of the first image and the second image is generated from data acquired by a multi-echo pulse sequence composed of a plurality of echo acquisition parts following one excitation pulse;
    the first image is generated from first data acquired in a first echo acquisition part in which a rephasing gradient pulse for suppressing phase change due to the flow is applied; and
    the second image is generated from second data acquired in a second echo acquisition part in which a dephasing gradient pulse for enhancing phase change due to flow is applied.

6. The MRI apparatus according to claim 1, wherein the processing circuitry is configured to distinguish between a region of non-flowing microbleeds and a region of flowing blood excluding the microbleeds by distinguishing difference in the flow.

7. The MRI apparatus according to claim 6, wherein the processing circuitry is configured to
    calculate a flow phase component for each pixel of the second image by using the first phase, the flow phase component having been mainly affected by the flow included in the second phase,
    determine a pixel, the flow phase component of which is smaller than a predetermined value, as a pixel belonging to non-flowing microbleeds, and
    determine a pixel, the flow phase component of which is equal to or larger than the predetermined value, as a pixel belonging to flowing blood excluding the microbleeds.

8. The MRI apparatus according to claim 6, wherein the processing circuitry is configured to
generate a first susceptibility image, in which each pixel value is a first susceptibility calculated from each pixel of the first image,
generate a second susceptibility image, in which each pixel value is a second susceptibility calculated from each pixel of the second image,
calculate susceptibility deviation for each pixel by performing subtraction processing between the first susceptibility of the first susceptibility image and the second susceptibility of the second susceptibility,
determine a pixel, susceptibility deviation of which is smaller than a predetermined value, as a pixel belonging to non-flowing microbleeds, and
determine a pixel, susceptibility deviation of which is equal to or larger than the predetermined value, as a pixel belonging to flowing blood excluding the microbleeds.

9. The MRI apparatus according to claim 1, wherein the third image is an image generated by the MRI apparatus including the first image and the second image or is an image generated by an apparatus other than the MRI apparatus.

10. An MRI apparatus comprising:
a memory configured to store a predetermined program; and
processing circuitry configured, by executing the predetermined program, to
generate a first image having a first phase affected by susceptibility,
generate a second image having a second phase affected by both of the susceptibility and flow,
generate a third image, in which both of an artery and a vein are depicted with high contrast with respect to a stationary background, by using the first image and the second image, and
distinguish between the artery and the vein depicted in the third image by using a value of susceptibility calculated from the first phase or by using a value of the first phase.

11. The MRI apparatus according to claim 10, wherein the first image is generated from first data acquired by a first pulse sequence in which a rephasing gradient pulse for suppressing phase change due to the flow is applied.

12. The MRI apparatus according to claim 10, wherein the second image is generated from second data acquired by a second pulse sequence in which a dephasing gradient pulse for enhancing phase change due to the flow is applied.

13. The MRI apparatus according to claim 11, wherein the second image is generated from second data acquired by a second pulse sequence in which a dephasing gradient pulse for enhancing phase change due to the flow is applied.

14. The MRI apparatus according to claim 10, wherein:
each of the first image and the second image is generated from data acquired by a multi-echo pulse sequence composed of a plurality of echo acquisition parts following one excitation pulse;
the first image is generated from first data acquired in a first echo acquisition part in which a rephasing gradient pulse for suppressing phase change due to the flow is applied; and
the second image is generated from second data acquired in a second echo acquisition part in which a dephasing gradient pulse for enhancing phase change due to the flow is applied.

15. The MRI apparatus according to claim 10, wherein the processing circuitry is configured to distinguish between the artery and the vein by using at least one of an absolute value of susceptibility calculated from the first phase and positive/negative sign of the susceptibility calculated from the first phase.

16. The MRI apparatus according to claim 10, wherein the processing circuitry is configured to distinguish between the artery and the vein by using at least one of an absolute value of the first phase and positive/negative sign of the first phase.

17. An MRI apparatus comprising:
a memory configured to store a predetermined program; and
processing circuitry configured, by executing the predetermined program, to
generate a first image having a first phase affected by susceptibility,
generate a second image having a second phase affected by both of the susceptibility and flow,
distinguish between non-flowing microbleeds and flowing blood excluding the microbleeds in a third image, in which the non-flowing microbleeds and the flowing blood are depicted, by using the first phase and the second phase or by using a value calculated from the first phase and a value calculated from the second phase.

* * * * *